US008466695B2

(12) United States Patent
Chiang et al.

(10) Patent No.: US 8,466,695 B2
(45) Date of Patent: Jun. 18, 2013

(54) CORROSION MONITORING OF CONCRETE REINFORCEMENT BARS (OR OTHER BURIED CORRODABLE STRUCTURES) USING DISTRIBUTED NODE ELECTRODES

(75) Inventors: Kuang-Tsan Kenneth Chiang, Helotes, TX (US); Lietai Yang, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 412 days.

(21) Appl. No.: 12/859,572

(22) Filed: Aug. 19, 2010

(65) Prior Publication Data

US 2012/0043981 A1 Feb. 23, 2012

(51) Int. Cl.
*G01R 27/08* (2006.01)

(52) U.S. Cl.
USPC ............................................. 324/700

(58) Field of Classification Search
USPC ............................................. 324/700
See application file for complete search history.

(56) References Cited

U.S. PATENT DOCUMENTS

| | | | | |
|---|---|---|---|---|
| 2,947,679 | A * | 8/1960 | Marsh et al. ................ | 204/404 |
| 3,980,542 | A * | 9/1976 | Winslow et al. ............ | 204/404 |
| 4,080,565 | A * | 3/1978 | Polak et al. ................ | 324/71.1 |
| 4,133,734 | A * | 1/1979 | Polak et al. ................ | 204/404 |
| 4,426,618 | A * | 1/1984 | Ronchetti et al. ......... | 324/700 |
| 4,703,253 | A * | 10/1987 | Strommen ................ | 324/700 |
| 4,703,255 | A * | 10/1987 | Strommen ................ | 324/700 |
| 4,861,453 | A * | 8/1989 | Matsuoka et al. ......... | 204/404 |
| 4,927,503 | A * | 5/1990 | Polly ........................ | 205/776.5 |
| 5,015,355 | A | 5/1991 | Schiessl | |
| 5,069,774 | A * | 12/1991 | Hladky et al. ............. | 204/404 |
| 5,259,944 | A * | 11/1993 | Feliu et al. ................ | 204/404 |
| 5,366,670 | A * | 11/1994 | Giner et al. ................ | 205/83 |
| 5,403,550 | A * | 4/1995 | Wietek ..................... | 422/53 |
| 5,712,559 | A * | 1/1998 | Moore et al. .............. | 324/71.1 |
| 5,792,337 | A * | 8/1998 | Padovani et al. .......... | 205/775.5 |
| 5,855,721 | A * | 1/1999 | Monteiro et al. .......... | 156/274.4 |
| 6,281,671 | B1 * | 8/2001 | Schiessl et al. ............ | 324/71.1 |
| 6,387,244 | B1 * | 5/2002 | Lyublinski ................ | 205/734 |
| 8,111,078 | B1 * | 2/2012 | Yang et al. ................ | 324/700 |

(Continued)

FOREIGN PATENT DOCUMENTS

JP 63090753 * 4/1988

OTHER PUBLICATIONS

Miranda et al., Several questions aboutelectrochemical rehabilitation methods for reinforced concrete structures, Aug. 2006, pp. 2176-2178.*

(Continued)

*Primary Examiner* — Jermele M Hollington
*Assistant Examiner* — Demetrius Pretlow
(74) *Attorney, Agent, or Firm* — Chowdhury & Georgakis PC; Ann C. Livingston (57) ABSTRACT

Systems and methods for real time detection of corrosion of rebars embedded in a concrete structure. Test bars are selected for corrosion testing purposes, and may or may not also be part of the concrete reinforcement structure. These test bars are coated, and exposed sections of these test bars form a network of node electrodes. Electrical measurement from a counter electrode near a node electrode provides an indication of corrosion at that node electrode. Using a system of node electrodes and counter electrodes, a large concrete area may be monitored, and if corrosion is indicated, a methodical selection of electrodes can be used to locate the corrosion. The same concepts may be applied to detect corrosion in buried structures, such as pipelines and tanks.

18 Claims, 7 Drawing Sheets

U.S. PATENT DOCUMENTS

| | | | |
|---|---|---|---|
| 2002/0057097 A1* | 5/2002 | Kelly et al. | 324/700 |
| 2003/0011387 A1* | 1/2003 | Trejo et al. | 324/700 |
| 2006/0125480 A1* | 6/2006 | Srinivasan et al. | 324/376 |
| 2010/0108510 A1* | 5/2010 | Hill | 204/404 |
| 2010/0300184 A1* | 12/2010 | Wayman et al. | 73/73 |

OTHER PUBLICATIONS

Feliu et al., A new method for in-situ measurementof electrical resistivityof reinforced concrete, Jul. 1996, pp. 362-365.*

* cited by examiner

CORROSION MONITORING OF CONCRETE REINFORCEMENT BARS (OR OTHER BURIED CORRODABLE STRUCTURES) USING DISTRIBUTED NODE ELECTRODES

TECHNICAL FIELD OF THE INVENTION

This invention relates to measuring corrosion of embedded concrete reinforcement bars (rebars) or other corrodible structures, and more particularly to performing such measurements using embedded metal bars with distributed node electrodes.

BACKGROUND OF THE INVENTION

A major cause of failure of concrete structures is corrosion of their reinforcement metal. The corrosion rate of embedded reinforcement bars (rebars) is an important parameter in assessing the remaining life of a concrete structure and the risk of its failure.

Efforts have been made to use electrochemical methods to measure the corrosion rate of rebars in concrete structures. However, these methods are challenging because the measurement area of the metal is difficult to define. When an electrochemical measurement is attempted from the rebar through a counter electrode, the measured current may not only be from corrosion reaction on metal near the counter electrode, but also from corrosion reactions occurring far away from the counter electrode. It is difficult to determine the corroding area that is contributing to the measured current, and thus difficult to measure a corrosion rate.

The concept of a guarded ring electrode for concrete-embedded rebar has been used to confine the current from the counter electrode to a certain area of the rebar. In a guarded ring electrode system, the counter electrode is surrounded by a large ring electrode, and both are flush mounted in an insulator. During measurement, the sensing surfaces of the flush-mounted counter electrode and guarded ring electrode are placed onto the concrete surface near the rebar and the rebar is used as the working electrode. The guarded ring electrode and the counter electrode are controlled at the same potential against the rebar, and the currents from the two electrodes to the rebar are measured separately. Because the guarded ring electrode is relatively large and creates a near-parallel electrical field around the counter electrode, the current from the counter electrode is confined to a window corresponding to the surface area of the counter electrode. Therefore, the total surface area of the rebar that is responsible for the current measured from the counter electrode is the area within the window of the counter electrode. This concept works well for simple structures such as a single rebar with a known diameter underneath the counter electrode, but is not accurate for complicated structures with many rebars connected together.

Because of the difficulties in measuring the corrosion rate of actual rebars, probes made of surrogate materials are often used to estimate the corrosion rate of the actual rebars. However, unless the probes are embedded in the concrete at the same time as the rebar, and have similar corrosion susceptibility, and have a similar corrosive environment, the corrosion rate of the probe may not be the same as the corrosion rate of the concrete rebar. In addition, corrosion probes are usually operated independently with dedicated electronic instruments and can only be installed in a limited number of locations in a concrete structure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to systems and methods for real time detection of corrosion of rebars embedded in a concrete structure. Embedded rebars (or other metal bars), are used as test bars for corrosion testing purposes, and may or may not also be part of the concrete reinforcement structure. These test bars have an electrically insulating coating, and exposed sections of these test bars form a network of node electrodes. Electrical measurement from a counter electrode near a node electrode provides an indication of corrosion at the node electrode. Using a system of node electrodes and counter electrodes, a large concrete area may be monitored, and if corrosion is indicated, a methodical selection of electrodes can be used to locate the corroding electrodes and assess the quantitative corrosion rate on the electrode(s).

Corrosion Detection Using Node Electrodes and Counter Electrode on Surface

Figure 1:
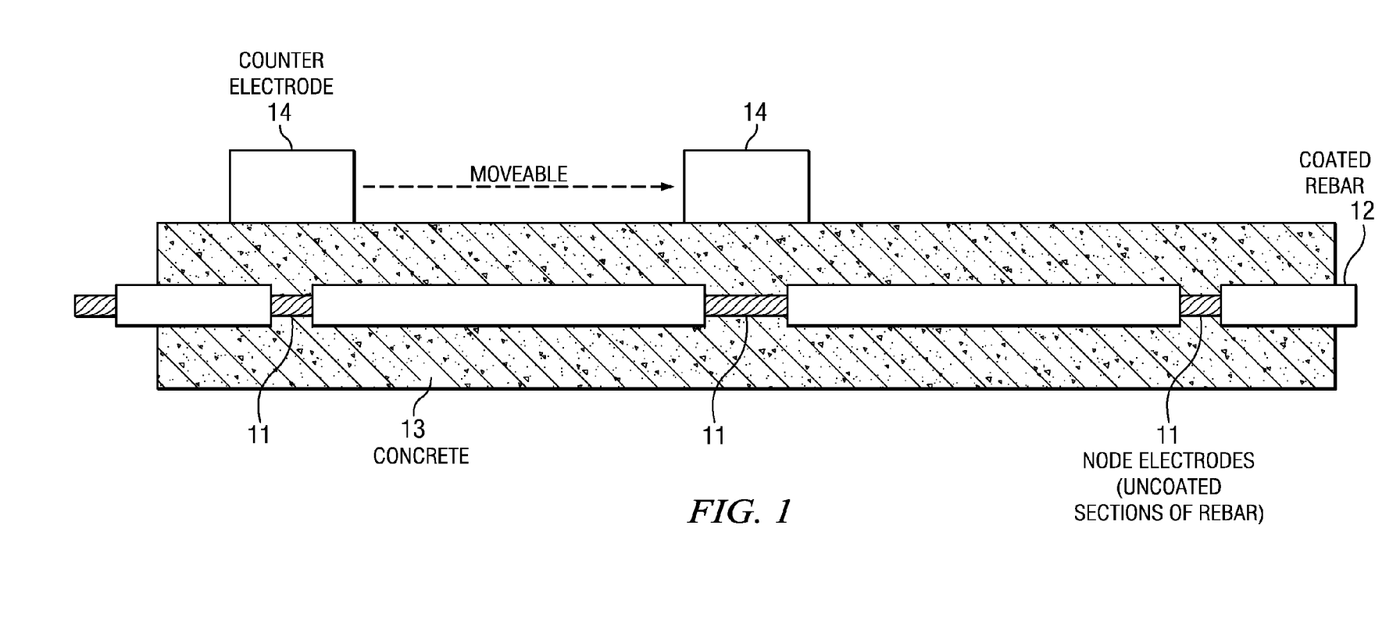
FIG. 1 is a simple illustration of the concept of using node electrodes on a length of rebar in concrete.

FIG. 1 is a simple illustration of using node electrodes 11 on a single length of test bar 12 embedded in concrete 13. It is assumed that the concrete 13 is part of a larger structure also having embedded rebar (not shown), typically uncoated and subject to corrosive influences.

The test bar 12 is coated with an electrically insulating material, such that only selected sections (preferably evenly distributed along the axial direction) are exposed to the concrete. These sections are the working (node) electrodes 11. Each exposed section has a well-defined surface area for corrosion rate measurement using a conventional electrochemical technique, such as a linear polarization resistance (LPR) or the zero-resistance ammetry (ZRA) technique.

The collection of the exposed sections forms the network of node electrodes 11. The node electrodes 11 of the test bar 12 simulate uncoated rebars (or coating-failed sections of coated rebar) in terms of corrosion behavior. This is because the test bar 12 used for the working (node) electrodes 11 is surrounded by the same concrete and subject to the same environment as the bare (structural) rebar.

It should be understood that although this description is written in terms of rebar in concrete, equivalents are possible for both rebar and concrete. In general, "rebar" is used in a general sense to mean any corrodible metal embedded in concrete (or other building material) and having a bar-like or pipe-like geometry. Equivalents for "concrete" may include other materials having resistivity properties as favorable or more favorable for purposes of the methods described herein.

It should be further understood that the use of "rebar" for the network of node electrodes is a logical selection of material because it is bare structural rebar whose corrosion is of interest. However, other metals could be used for the working electrodes, and they will typically have a geometry, such as long bars, that permits them to be embedded into the concrete as a grid. Typically, the test bar 12 will have similar corrosive tendencies as the rebar (or other metal) whose corrosion is of interest. For clarity, rebars used for working electrodes, such as test bar 12, are referred to herein as "coated" or "test" rebars, to be distinguished from the structural rebars, which are typically uncoated and are thus referred to as "uncoated" or "bare" rebars.

A counter electrode 14, as required for electrochemical measurements (such as with the LPR method), may be placed on the concrete surface above a node electrode 11 for the measurement. For the LPR method, a wetting agent, such as a wet sponge (not shown), also may be placed above a node electrode 11. The counter electrode 14 may be moved across the surface of the concrete, above different node electrodes 11.

Depending on the type of corrosion analysis method used, a reference electrode may also be used. The use of two electrodes (working and counter) versus three electrodes (with a reference electrode) should be understood by those skilled in the art of electrochemical systems. The counter electrode and the reference electrode near a particular node are only required during the measurement and can be removed from the location after a measurement is completed.

The spacing (distance) between neighboring node electrodes 11 is such that the charge from the counter electrode 14 preferentially flows to the single node electrode 11 that is closest to the counter electrode 14. This allows calculation of the corrosion rate on the node electrode 11, using known data analysis techniques. The ionic resistivity of concrete is often extremely high (>1000 ohms), which helps ensure that most of the charge collected at a counter electrode 14 will be from the node electrode 11 located nearest to the counter electrode 14 if there is no uncoated long rebar near both the node electrode being measured and other node electrodes. Such uncoated rebar may carry the charge from the node electrode to the other node electrodes in the form of stray current.

Test bars, such as test bar 12, may be made from rebar, and installed during construction of a new system or during repair of a failed section of an existing concrete structure. The node electrodes 11 installed during the repair simulate the repaired rebars in terms of corrosion. The test bars 12 for the node electrodes 11 can serve not only as working electrodes for corrosion monitoring, but also for the reinforcement of the concrete structure. The quality of the electrically insulating coating should be such that it will last the design life of the concrete structure.

Use of Bare Rebars as Counter Electrodes for Corrosion Monitoring

Figure 2:
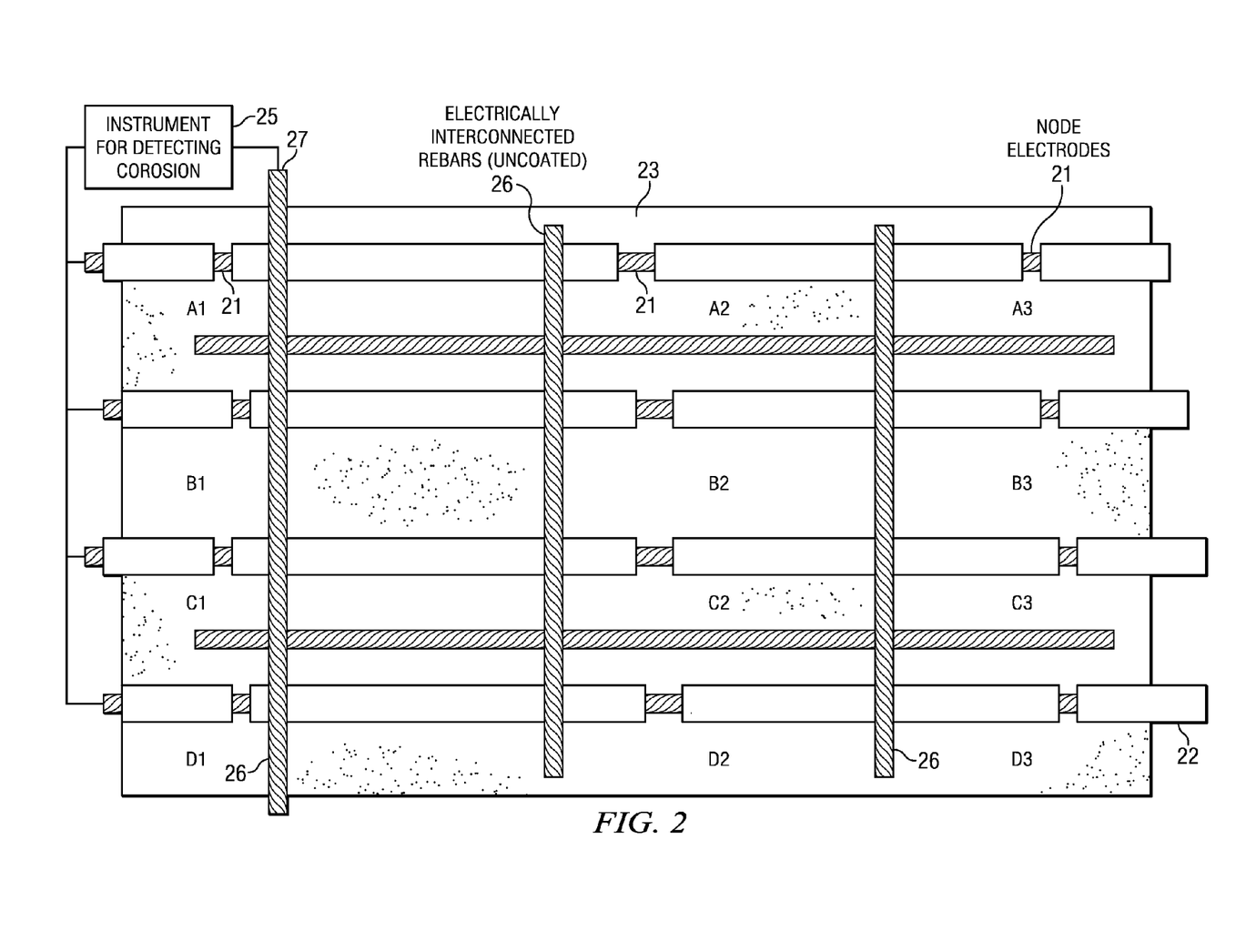
FIGS. 2 and 3 illustrate how multiple metal bars can be connected together to form a network of node electrodes.
Figure 3:
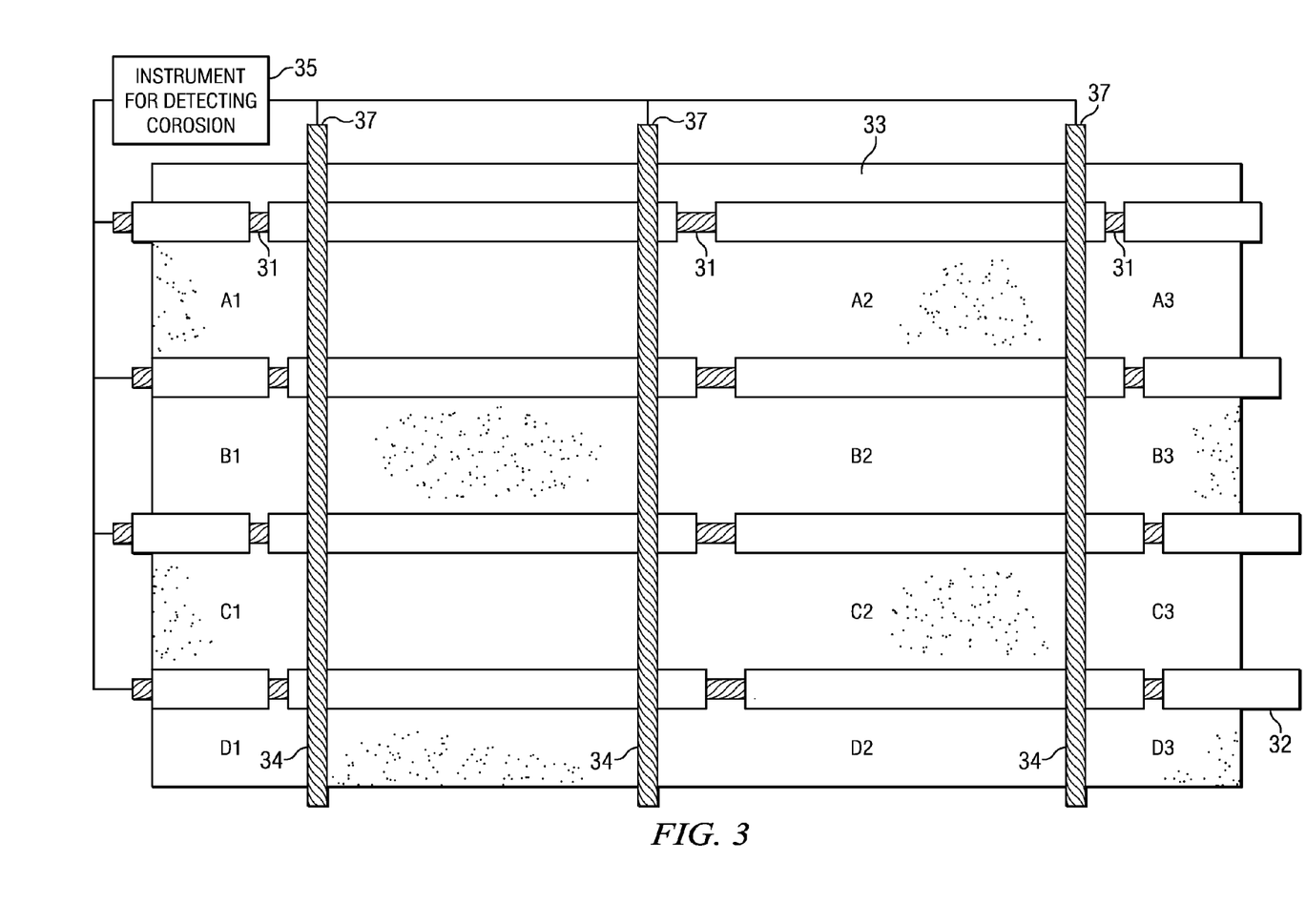

FIGS. 2 and 3 illustrate how multiple coated metal bars having exposed nodes (such as test bar 12 of FIG. 1) can be used to form a network of node electrodes. The network of node electrodes, together with uncoated rebars used as counter electrodes, can be used to monitor corrosion of other rebars within the same concrete.

In FIG. 2, rows of coated test bars 22, having exposed node electrodes 21, are embedded within the concrete 23. These test bars 22 are electrically connected (such as with a wire lead) to a measurement instrument 25. The node electrodes 21 are the working electrodes.

The concrete also has embedded uncoated rebars 26, used for structural purposes in a normal manner, but electrically interconnected in a cross-grid within the concrete. In typical concrete structure, an electrical interconnection occurs normally, as a result of the rebars being secured together with tie wires or the like at the cross points of the grid.

The measurement instrument 25 is also electrically connected to the uncoated grid of rebars 26. The grid of rebars 26 has a connection point 27 at the concrete surface for this purpose. During monitoring, these uncoated rebars 26 act as counter electrodes.

As stated above, various electrochemical methods may be used for analyzing the measurement data, thus measurement instrument 25 may have appropriate circuitry or programming for whatever method is used. Alternatively, measurement instrument 25 may be a simple data gathering device for acquiring measurement data for analysis by other equipment.

Because the corrosion rate of rebar in concrete is typically quite low, the measurement instrument 25 should indicate a low corrosion signal, even though the signal is from a large number of node electrodes all connected together for input on one channel. The use of only one input signal simplifies the need for signal processing and transmitting. It also greatly reduces the cost for effectively monitoring corrosion over large areas of a concrete structure.

For corrosion monitoring, a baseline response signal received at instrument 25 is noted. If this signal increases above a specified threshold, a potential corrosion area is deemed to be identified. If this occurs, the test bars 22 can be electrically separated (to reduce the number of nodes) to better locate the corrosion area(s) whose electrical response indicates corrosion.

In FIG. 3, as in FIG. 2, rows of test bars 32 are embedded in the concrete. In addition, columns of uncoated rebars 34 are electrically isolated from each other. Each rebar 34 has a connection point 37 at the surface of the concrete, for connection to the measurement instrument 35, and each serves as a counter electrode.

Figure 4:
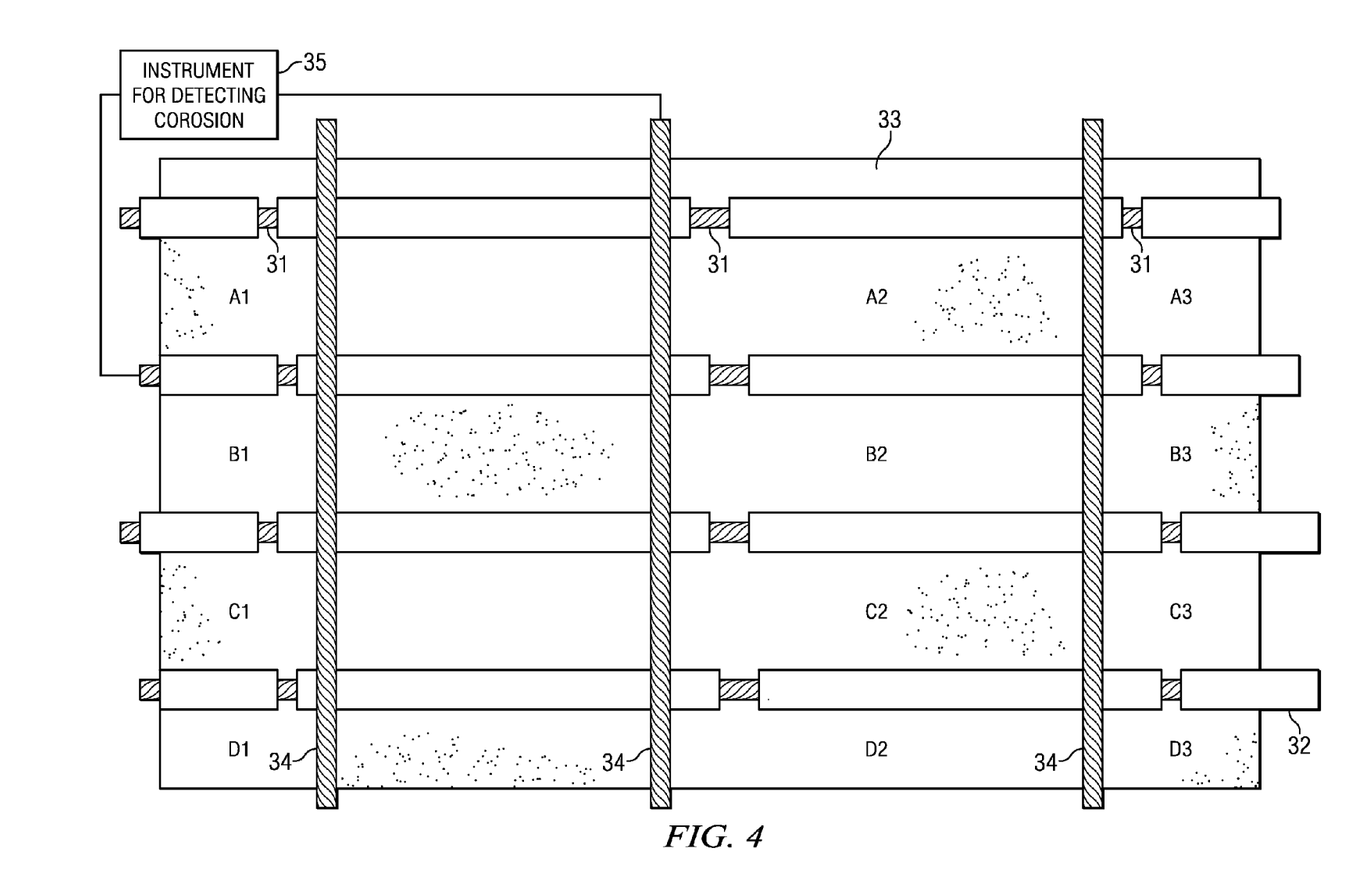
FIG. 4 illustrates how the corrosion rate at a given node can be measured by connecting a measurement instrument only to the node electrode bar and the counter electrode bar corresponding to the particular node.

As illustrated in FIG. 4, when electrically separated counter electrode bars 34 are used (as in FIG. 3), the corrosion rate at a given node electrode 31 can be measured by connecting the instrument 35 only to the test bar 32 and the counter electrode bar 34 corresponding to the particular node. Specifically, FIG. 4 illustrates measurement at Node B2, when the measurement instrument 35 is connected to a single test bar (Row 2) and a single counter electrode rebar (Column 2). Because the counter electrode rebar can be placed close to the node electrodes, this approach minimizes the potential effect of stray current by uncoated long rebar (or several electrically connected rebars) that may electrically connect the vicinity of several node electrodes together.

Node Spacing

As stated above, for proper operation, current from the counter electrode should mostly flow into the node electrode that is closest to the counter electrode. In other words, the current from the counter electrode flowing into the neighboring node electrodes must be small or negligible compared to the current following into the closest node electrode. Therefore, the distance between the node electrodes should be such that the concrete resistance has significant effect on the measured uncompensated corrosion rate, or the measured uncompensated polarization resistance is dominated by the concrete resistance.

Figure 5:
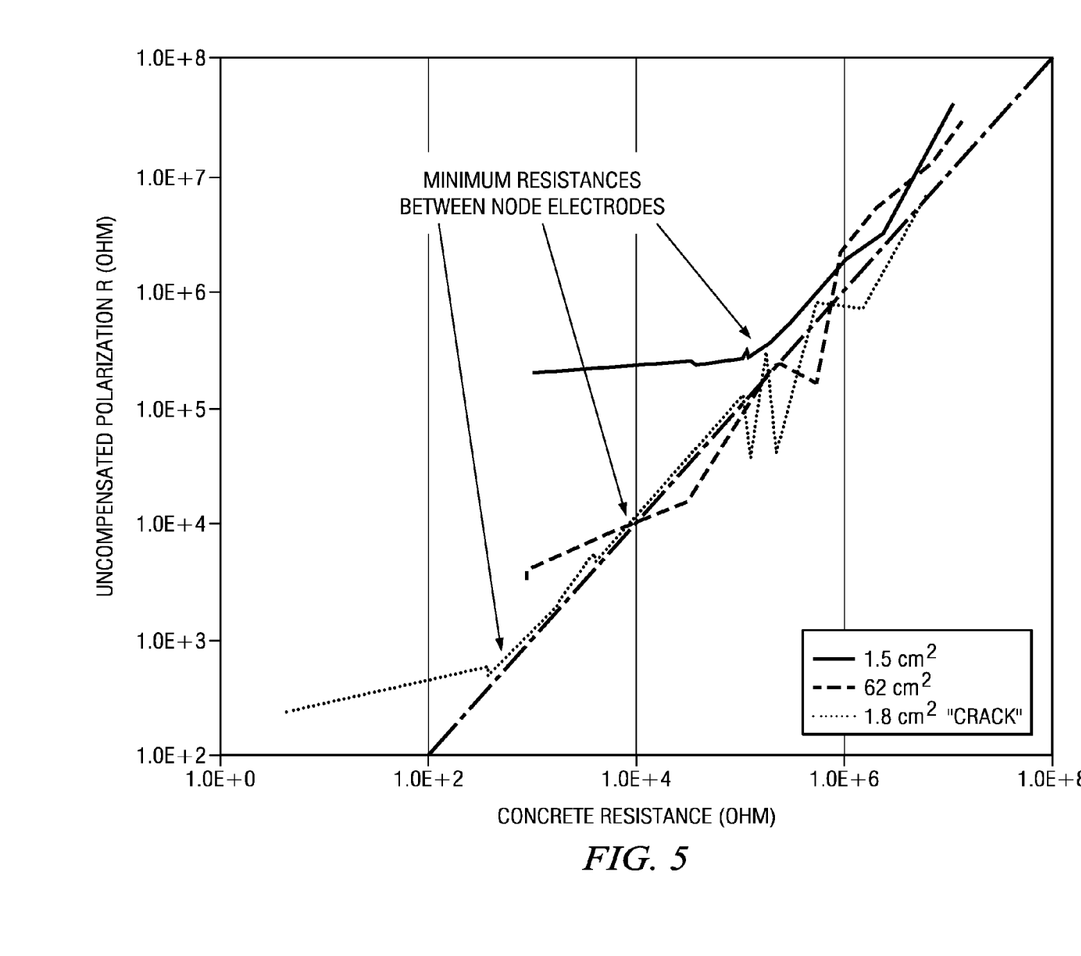
FIG. 5 illustrates how proper node spacing can be quantitatively determined.

FIG. 5 illustrates how proper node spacing can be quantitatively determined. More specifically, FIG. 5 plots polarization resistance as a function of concrete resistance measured between a working electrode and a reference electrode. Measurements from three types of electrodes are plotted: from electrodes having surface areas of 1.5 cm$^2$ and 62 cm$^2$ in embedded in concrete, and from an electrode having a 1.8 cm² surface area but placed in a seawater-filled crack in the concrete for comparison purposes.

"Polarization resistance" values are a basis for deriving corrosion current and corrosion rate, according to the following formula:

$$I_{corr}=26/R_p,$$

where $I_{corr}$ is the corrosion current (mA), 26 is an assumed Stern-Geary constant, also called B value (mV), and $R_p$ is the polarization resistance (ohm). The measured $R_p$ is uncompensated polarization resistance, which is the sum of the electrochemical polarization resistance at the electrode interface and the concrete resistance.

When the interface electrochemical polarization resistance (related to the corrosion rate) is low compared to the concrete resistance, the measured uncompensated polarization resistance equals the concrete resistance. This is shown by the 45 degree dashed line in FIG. 5. When the concrete resistance decreases, the polarization resistance purely due to corrosion became dominant and began to deviate from the 45 degree straight line.

Using plots such as FIG. 5, it can be demonstrated that the uncompensated polarization resistance from electrodes with smaller surface areas or those that have a lower corrosion rate begin to deviate from the straight line at a higher concrete resistance. The uncompensated polarization resistance from the electrodes with larger surface area or those that have a higher corrosion rate begin to deviate from the straight line at a lower concrete resistance. As the concrete resistance decreases further, the electrochemical polarization resistance due to corrosion becomes a limiting factor and could not be decreased further.

Thus, when the measured uncompensated polarization resistance deviates from the 45 degree line, the uncompensated polarization resistance is dominated by the electrochemical polarization resistance; when the uncompensated polarization resistance is on the 45 degree dashed line, the uncompensated polarization resistance is dominated by the concrete resistance. Therefore, the minimum distance between the neighboring node electrodes should be such that the measured uncompensated polarization resistance starts to deviate from the 45 degree line.

FIG. 5 shows that the minimum concrete resistances between the neighboring node electrodes are 100,000, 5,500 and 370 ohms for the 1.5 cm² electrode and 62 cm² electrode in concrete, and 1.8 cm² electrode in cracks filled with seawater, respectively. According to FIG. 5, if the surface area of the node electrode is small, the distance between the neighboring electrodes must be large; if the surface area of the node electrode is large, the neighboring electrodes can be close to each other. On the other hand, if the corrosivity of the environment for the metal is low (low corrosion rate such as carbon steel in concrete), the distance between any two of the neighboring electrodes must be large; if the corrosivity of the environment for the rebar is high (high corrosion rate such as carbon steel in a concrete crack filled with seawater), the distance between the neighboring electrodes can be small. This is because a large surface area or a high corrosivity supports a larger current. High current can flow between the counter electrode and the node electrode that is immediately beneath the counter electrode because there is no significant concrete resistance effect. However, high current cannot flow between the counter electrode and the neighboring nodes which are relatively far away from the counter electrode because of the concrete resistance effect.

It should be mentioned that the criteria described above applies also to cases where there are uncoated rebars electrically connecting the vicinity of several node electrodes. The existence of such uncoated rebars near the node electrodes may produce stray current and reduce the effective concrete resistance between the node electrode under measurement and the other node electrodes.

Monitoring Applications

Figure 6:
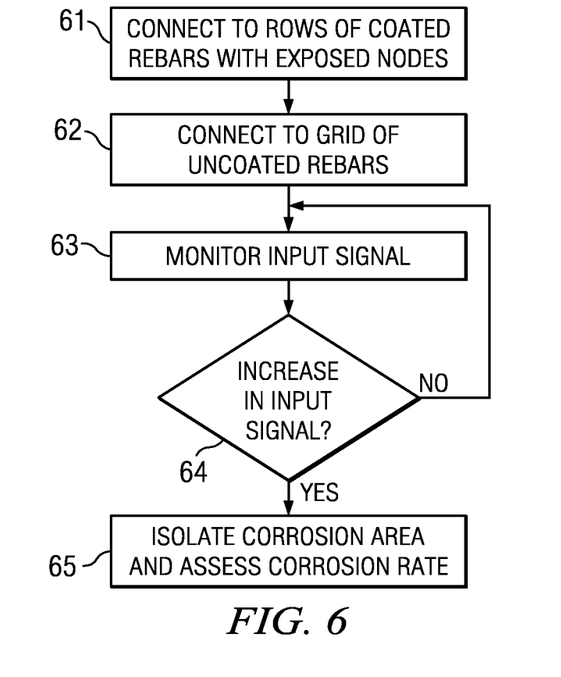
FIG. 6 illustrates a method of using distributed node electrodes to monitor for corrosion of rebars embedded in concrete, and to locate the corrosion.

FIG. 6 illustrates a method of using a network of node electrodes for monitoring corrosion of rebar in concrete, and if the monitoring indicates corrosion, for locating the problem area(s). As stated above, and as illustrated in FIGS. 2 and 3, for monitoring applications, a measurement instrument may be connected to all rebars serving as working electrodes and counter electrodes.

Step 61 is connecting the measurement instrument to a set of working electrodes. The working electrodes are exposed nodes on coated test bars, as described above. Typically, the test bars will be arranged in evenly spaced rows, with the node spacing designed as described above.

Step 62 is connecting the measurement instrument to a set of counter electrodes. The counter electrodes are either a grid (as in FIG. 2) or rows (as in FIG. 3) of bare rebars. For the "grid" configuration, the grid has a connection point for the measurement instrument that is accessible from the surface of the concrete. For the "row" configuration, each rebar serving as a counter electrode has a connection point. The rows of rebars serving as counter electrodes are arranged perpendicular to the rebars serving as working electrodes.

Step 63 is receiving and monitoring the cumulative (single channel) input signal from all electrodes. The area covered by the working electrodes and counter electrodes can be quite large, thus a large span of concrete can be monitored.

Step 64 is comparing the amplitude of the input signal to a reference value, that is, a value that would be expected if the uncoated rebar is not corroding or if the corrosion rate is low enough to be acceptable. If the input signal value does not exceed the reference value, no corrosion or acceptable corrosion is assumed.

If the input signal value does exceed the reference value, Step 65 is isolating the area(s) where the corrosion is occurring. For the "grid" configuration as shown in FIG. 2, measuring the corrosion signal from each test bar 22 with the grid of counter electrode 26 as counter electrode allows the identification of row(s) of the test bars that is/are more corroding. For the "grid" configuration as shown in FIG. 3, measuring the corrosion signal from each test bar 32 against a single counter electrode 36 (when the grid of counter electrodes is disconnected from each other) allows the identification of the exact node electrode that is corroding.

Once the location of the corrosion has been determined, further analytical corrosion testing methods can be used to determine the rate of corrosion. For configuration as shown in FIG. 4, the corrosion rate for the corroding node electrode can be obtained by using the corresponding column of the counter electrode 34 as the counter electrode. For the configuration as shown in FIG. 2, a separate movable counter electrode (FIG. 1) may be used to assess the corrosion rate of each node electrode.

Figure 7:
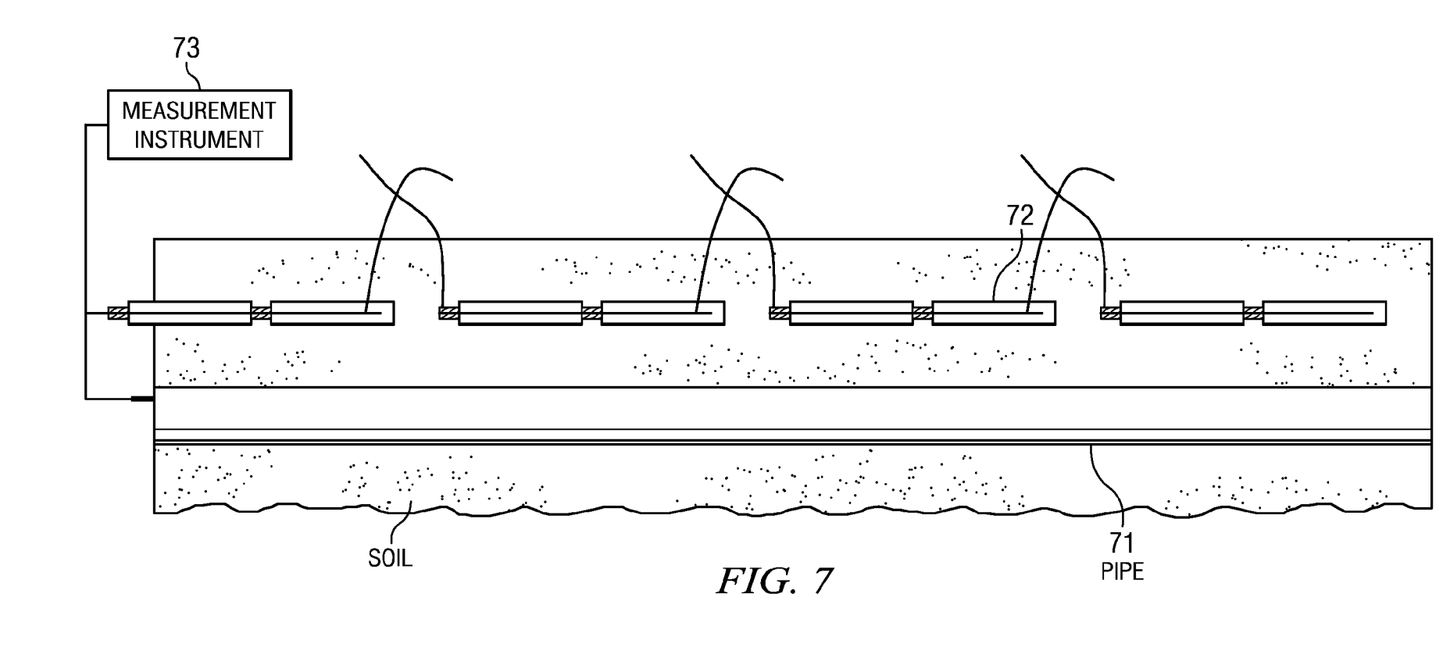
FIG. 7 illustrates how the method is also applicable for the assessment of external corrosion of metal structures buried in soil.

FIG. 7 illustrates how the above-described method is also applicable for the assessment of external corrosion of metal structures buried in soil. In the embodiment of FIG. 7, the node electrodes are being used to detect corrosion on a pipeline 71. A linear line 72 of test node electrodes may be buried along with the pipe. In the embodiment of FIG. 7, sections of rebar (or similar material) having node electrodes are electrically linked to follow the length of the pipe 71. The pipe 71 may be used as counter electrode during the detection phase. The pipe 71 and the electrode line 72 are connected to a measurement instrument 73. If a high corroding area is identified during the detection phase, a separate temporary counter electrode may be inserted near the corroding node electrode to assess the quantitative corrosion rate.

The same concepts could be applied to other buried structures, including planar structures such as buried tanks. Rows of electrode lines, such as line 72, could be placed at an appropriate distance from the outer tank surface. The spacing of the electrode line from the structure (pipeline, tank, or other) is determined in a manner similar to that described above, except that the electrode lines are embedded (buried) in soil, sand, or other earth surface material rather than concrete.

What is claimed is:

1. A method of detecting corrosion of rebars embedded in a building material made from concrete or other material having resistivity properties favorable or more favorable to electrochemical corrosion measurement, comprising:
    embedding in the same building material as the rebars, test bars made of the same material as the rebars or a material having similar corrosive tendencies;
    wherein each test bar is coated with an electrically insulating coating, except for one or more exposed sections located along the length of the test bar at locations other than or in addition to the ends of the test bar, such that each exposed section is operable as a node electrode;
    connecting at least one test bar to a corrosion measurement instrument;
    placing a counter electrode at a location near one of the node electrodes;
    receiving an input signal from the counter electrode at the measurement instrument;
    analyzing the input signal to determine if the signal indicates corrosion at the one of the node electrodes; and
    if the analyzing step indicates corrosion, using the location of the one of the node electrodes to determine the location of the corrosion.

2. The method of claim 1, further comprising placing a wetting agent under the counter electrode.

3. The method of claim 1, further comprising repeating the placing, receiving, and analyzing steps for a succession of counterelectrode locations and node electrodes.

4. A system for monitoring corrosion of rebars embedded in a building material made from concrete or other material having resistivity properties favorable or more favorable to electrochemical corrosion measurement, comprising:
    a working electrode network having at least one test bar made of the same material as the rebars or a material having similar or greater corrosive tendencies;
    wherein each test bar is coated with an electrically insulating coating, except for one or more exposed sections along the length of the test bar at locations other than or in addition to the ends of the test bar, such that each exposed section is operable as a node electrode;
    a counter electrode network having one or more rebars serving as counter electrodes, said rebars being embedded in the concrete in a plane parallel to that of the working electrode network but laid substantially perpendicular to the at least one test bar; and
    an electrical connection point at the surface of at least one of the rebars.

5. The system of claim 4, wherein the counter electrode network is a grid of electrically connected rebars, with at least one of said rebars having the connection point.

6. The system of claim 4, wherein the counter electrode network is columns of rebars, with each rebar having a connection point.

7. The system of claim 4, wherein the working electrode network has evenly spaced rows of test bars.

8. The system of claim 4, wherein the counter electrode network has rebars that are uncoated.

9. The system of claim 4, wherein the counter electrode network has rebars that are made from a material more corrodible than the test bars.

10. The system of claim 4, wherein the test bar is made from the same material as the rebars.

11. A method of monitoring for and locating corrosion of rebars embedded in a building material made from concrete or other material having resistivity properties favorable or more favorable to electrochemical corrosion measurement, comprising:
    embedding in the same building material as the rebars, rows of test bars made of the same material as the rebars or a material having similar corrosive tendencies;
    wherein each test bar is coated with an electrically insulating coating, except for one or more exposed sections along the length of the test bar at locations other than or in addition to the ends of the test bar, such that each exposed section is operable as a node electrode;
    selectively connecting a row of the test bars to a corrosion measurement instrument;
    selecting one or more rebars to serve as a counter electrode network;
    providing an electrical connection point at the surface of at least one of the rebars;
    receiving an input signal from the counter electrode network at the measurement instrument; and
    analyzing the input signal to determine if the signal indicates corrosion at any of the rebars;
    if the analyzing step indicates corrosion, using the location of the test bar and its node electrodes to locate the corrosion.

12. The method of claim 11, wherein the counter electrode network is a grid of electrically connected rebars, with at least one of said rebars having the connection point.

13. The method of claim 11, wherein the counter electrode network is columns of rebars, with each rebar having a connection point.

14. The method of claim 11, further comprising the step of separately connecting the test bars and the counter electrode rebars to locate a node electrode where corrosion is occurring.

15. The method of claim 11, wherein the test bars are made from the same material as the rebars.

16. A method of detecting corrosion of a buried metal structure, comprising:
    Burying in soil adjacent the structure, at least one test bar made of the same material as the structure or a material having similar corrosive tendencies;
    wherein each test bar is coated with an electrically insulating coating, except for one or more exposed sections along the length of the test bar at locations other than or in addition to the ends of the test bar, such that each exposed section is operable as a node electrode;
    connecting at least one test bar to a corrosion measurement instrument;
    placing a counter electrode at a location near a node electrode;
    receiving an input signal from the counter electrode at the measurement instrument; and
    analyzing the input signal to determine if the signal indicates corrosion at the node electrode;

if the analyzing step indicates corrosion, using the location of the test bar and its node electrodes to locate the corrosion.

17. The method of claim 16, wherein the structure is a pipeline and the test bar is placed along a length of the pipeline.

18. The method of claim 16, wherein the structure is planar in geometry, and multiple test bars are placed in rows spaced from the structure.

* * * * *